(12) United States Patent
Meyer et al.

(10) Patent No.: US 6,649,128 B1
(45) Date of Patent: Nov. 18, 2003

(54) ASSAY DEVICE PROCESSING INSTRUMENT

(75) Inventors: James Rudolf Meyer, Crumlin (GB); Ahti Kalevi Kansanaho, Crumlin (GB); Stephen Peter Fitzgerald, Crumlin (GB); Robert Ivan McConnell, Crumlin (GB); John Victor Lamont, Crumlin (GB); Bailin Cao, Crumlin (GB)

(73) Assignee: Randox Laboratories LTD, Crumlin (GB)

( * ) Notice: Subject to any disclaimer, the term of this patent is extended or adjusted under 35 U.S.C. 154(b) by 0 days.

(21) Appl. No.: 09/397,735

(22) Filed: Sep. 17, 1999

(30) Foreign Application Priority Data

Sep. 23, 1998 (EP) .............................. 98307706

(51) Int. Cl.⁷ ...................... G01N 21/00; G01N 31/00; G01N 33/00; G01N 15/06; G01N 33/48; G01N 35/02; B32B 27/04; B32B 27/12

(52) U.S. Cl. ........................... 422/63; 422/65; 422/64; 422/68.1; 422/50; 436/47

(58) Field of Search ..................... 422/65, 64, 50, 422/63, 68.1; 436/47

(56) References Cited

U.S. PATENT DOCUMENTS

| | | | |
|---|---|---|---|
| 4,403,687 A | | 9/1983 | Stevens et al. |
| 4,591,556 A | * | 5/1986 | Saxholm ........................ 435/33 |
| 4,692,308 A | * | 9/1987 | Riley et al. .................... 422/65 |
| 4,710,352 A | * | 12/1987 | Slaton et al. .................. 422/63 |
| 4,855,109 A | * | 8/1989 | Muraishi et al. ............... 422/63 |
| 4,857,272 A | * | 8/1989 | Sugaya ......................... 422/65 |
| 5,009,998 A | | 4/1991 | Chow et al. |
| 5,104,231 A | * | 4/1992 | Collier et al. ................ 366/208 |
| 5,154,889 A | | 10/1992 | Muraishi |
| 5,232,665 A | * | 8/1993 | Burkovich et al. ............ 422/65 |
| 5,240,678 A | * | 8/1993 | Litsche ......................... 422/64 |
| 5,360,597 A | * | 11/1994 | Jakubowicz et al. .......... 422/64 |
| 5,518,688 A | * | 5/1996 | Gianino ........................ 422/65 |
| 5,670,375 A | * | 9/1997 | Seaton et al. ................. 436/48 |
| 5,736,101 A | * | 4/1998 | Gianino ........................ 422/65 |

(List continued on next page.)

FOREIGN PATENT DOCUMENTS

| | | | | |
|---|---|---|---|---|
| EP | 0 497 019 A1 | * | 8/1992 | ......... G01N/35/02 |
| EP | 0 571 033 A1 | | 5/1993 | |
| EP | 0 733 905 A2 | | 9/1996 | |
| JP | 08029432 A | * | 2/1996 | |
| JP | 2002-22738 | * | 1/2002 | |
| WO | 0 802 413 A2 | | 11/1993 | |
| WO | WO 98/00697 | | 1/1998 | |

OTHER PUBLICATIONS

WO 93/12431 (PCT/US92/11133 Jun. 24 1993 Kelso et al.*
Beck, Shane, "Round and Round, Side to Side: Environmental Shakers/Incubators," The Scientist, vol. 12, No. 16, Aug. 1988, pp. 16–19.
"The ThermoPrep 3," HYPERION, web pages.

*Primary Examiner*—Arlen Soderquist
*Assistant Examiner*—Brian R. Gordon
(74) *Attorney, Agent, or Firm*—Oliff & Berridge, PLC

(57) ABSTRACT

An assay device processing instrument comprises a plurality of processing modules. A transport system transports an assay device to each processing module, the transport system being adapted to transfer the assay device from the transport system to the module to enable the transport system to transport another assay device while the first is processed by the processing module. A control system controls operation of the transport system such that each assay device is transferred between the modules in a predetermined sequence, and such that a number of assay devices can be processed in different modules simultaneously.

14 Claims, 15 Drawing Sheets

U.S. PATENT DOCUMENTS

| | | | |
|---|---|---|---|
| 5,736,102 A | * | 4/1998 | Seaton et al. .................. 422/65 |
| 5,762,874 A | * | 6/1998 | Seaton et al. .................. 422/65 |
| 5,798,084 A | * | 8/1998 | Seaton et al. .................. 422/65 |
| 5,807,523 A | | 9/1998 | Watts et al. |
| 5,849,247 A | * | 12/1998 | Uzan et al. ................... 422/65 |
| 5,966,309 A | * | 10/1999 | O'Bryan et al. ....... 364/478.13 |
| 5,985,215 A | * | 11/1999 | Sakazume et al. ............ 422/67 |
| 6,019,945 A | * | 2/2000 | Ohishi et al. .................. 422/65 |
| 6,106,781 A | * | 8/2000 | Rosenberg ................... 422/64 |
| 6,146,882 A | * | 11/2000 | Uematsu et al. ......... 435/303.1 |
| 6,261,521 B1 | * | 7/2001 | Mimura et al. ................ 422/67 |
| 6,296,809 B1 | * | 10/2001 | Richards et al. .............. 422/64 |

* cited by examiner

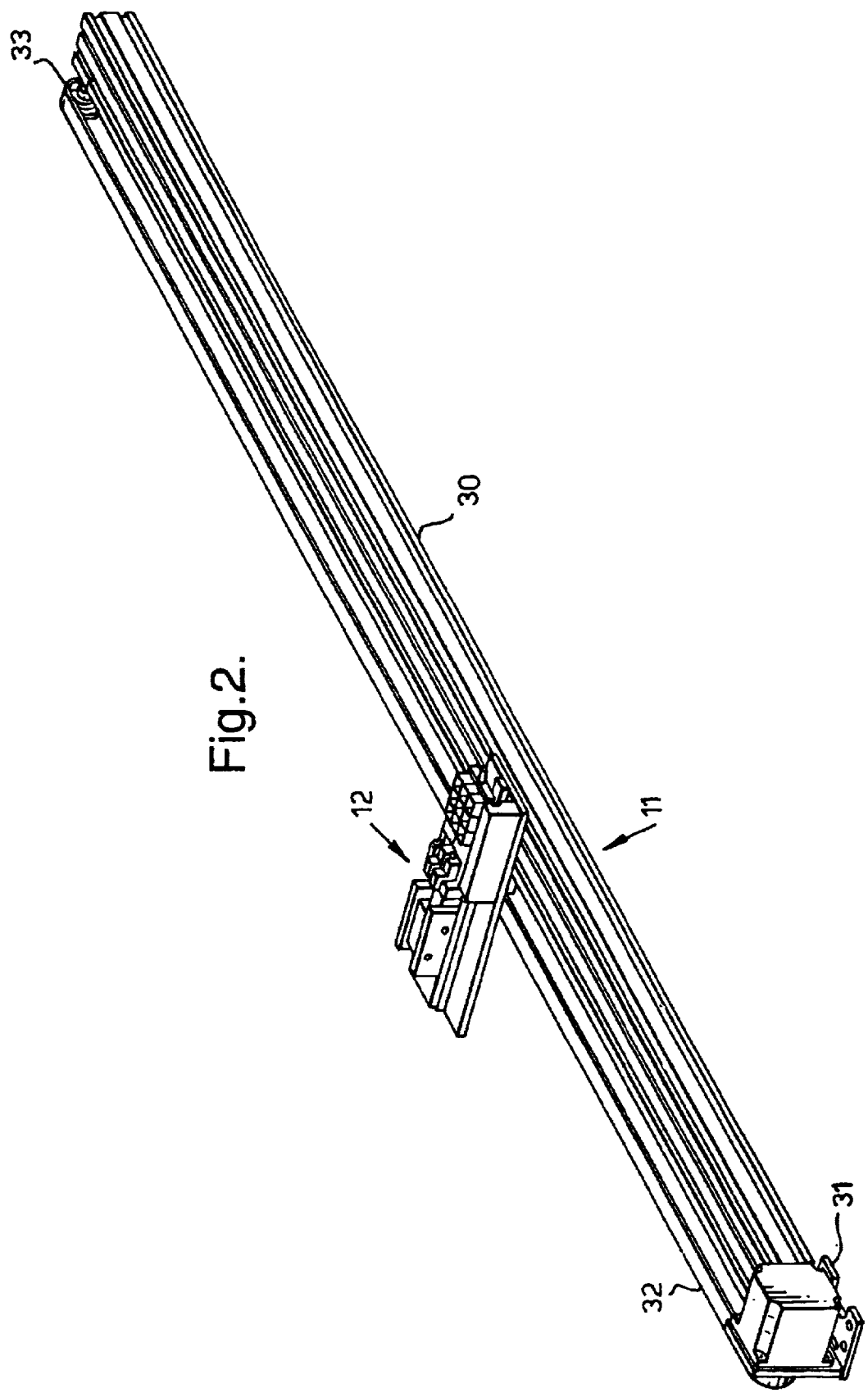

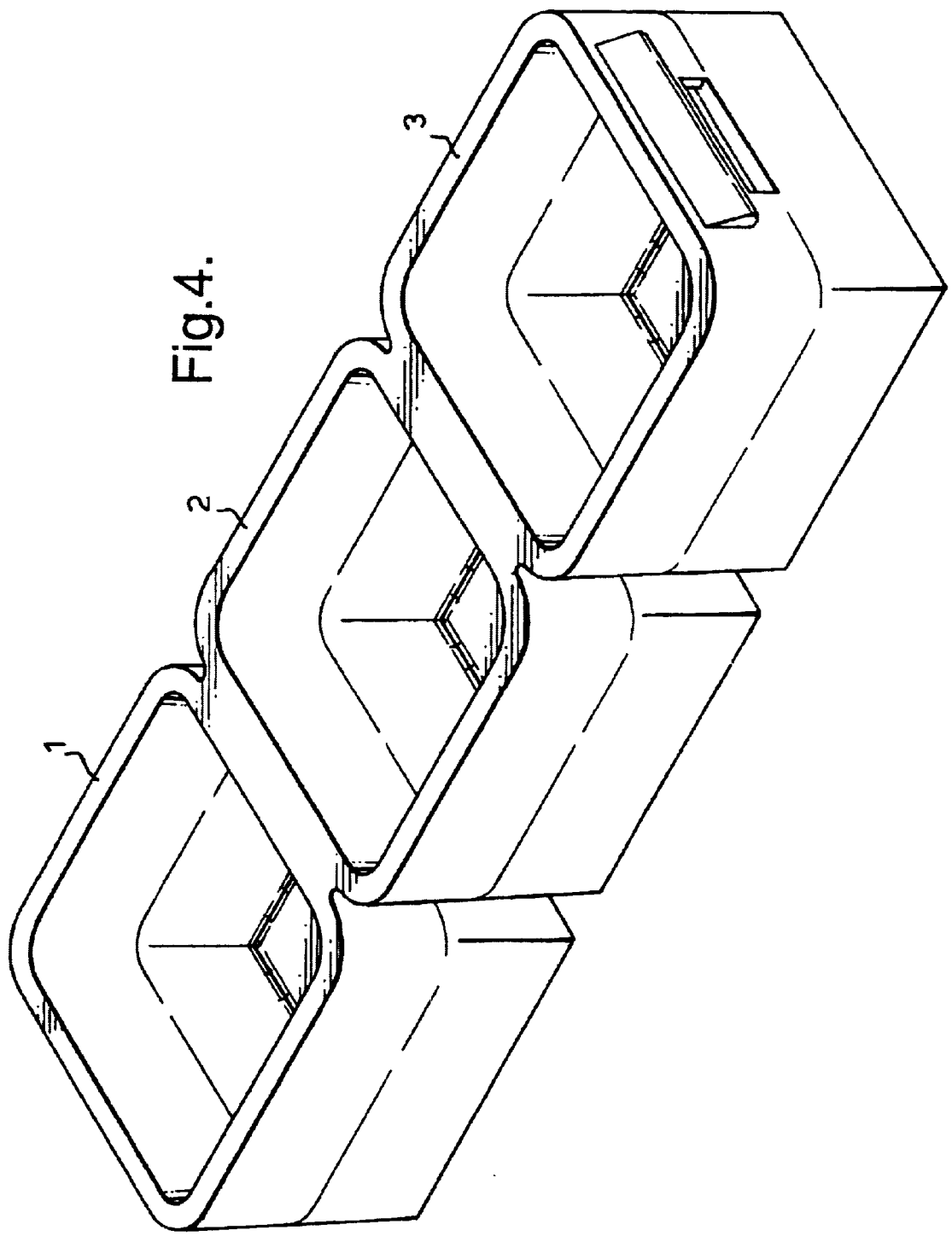

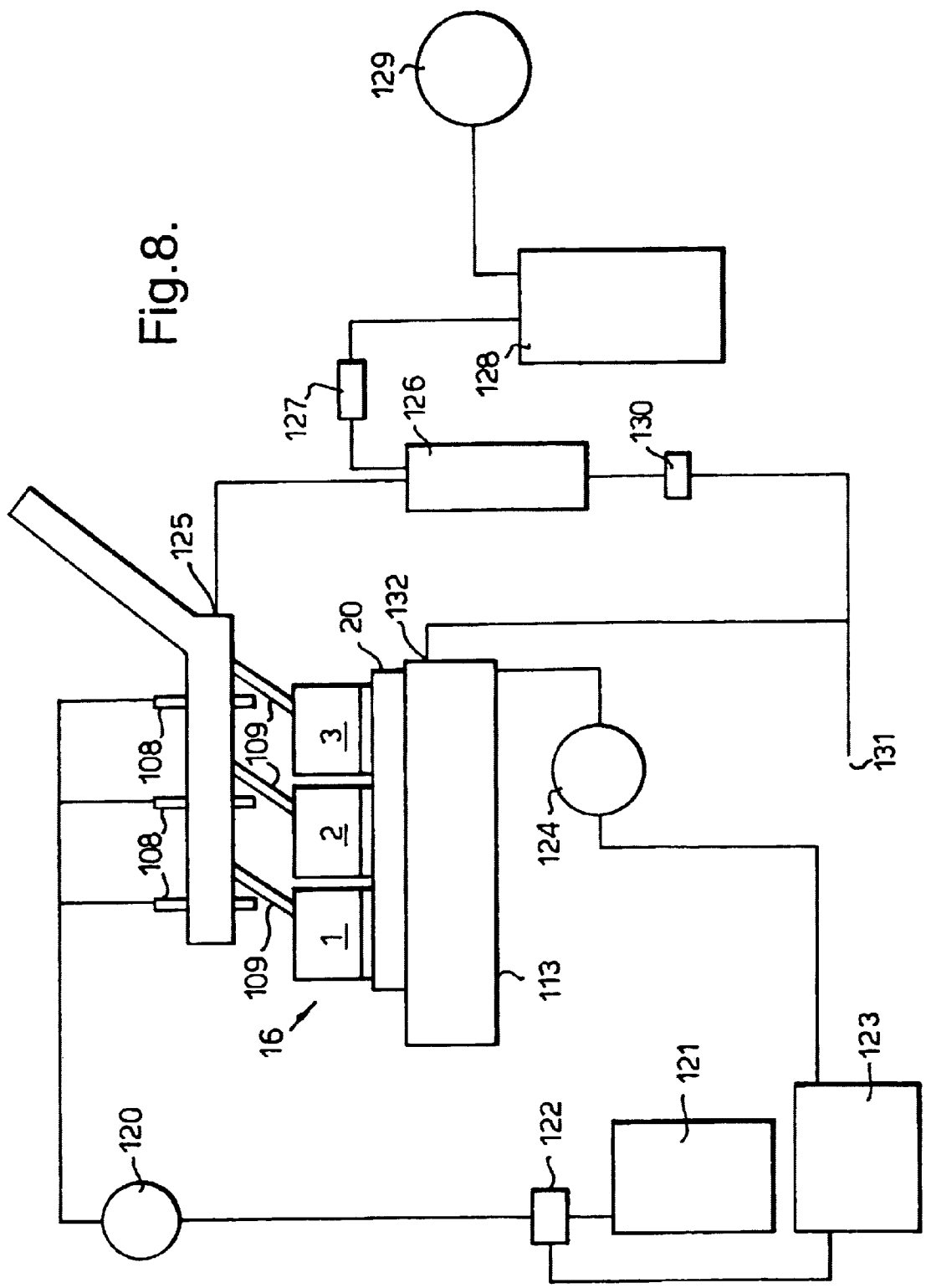

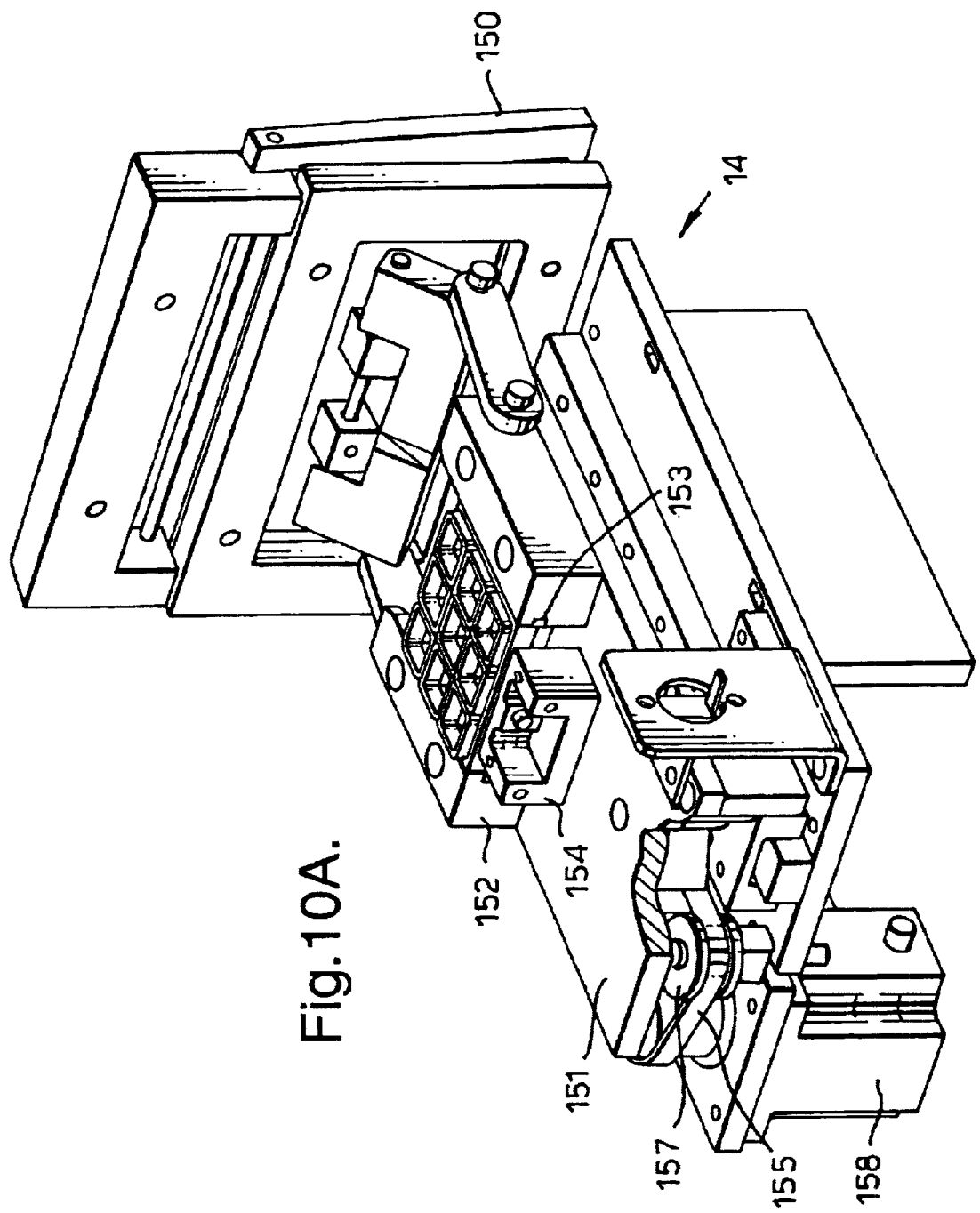

Fig.12.
Fig.13.
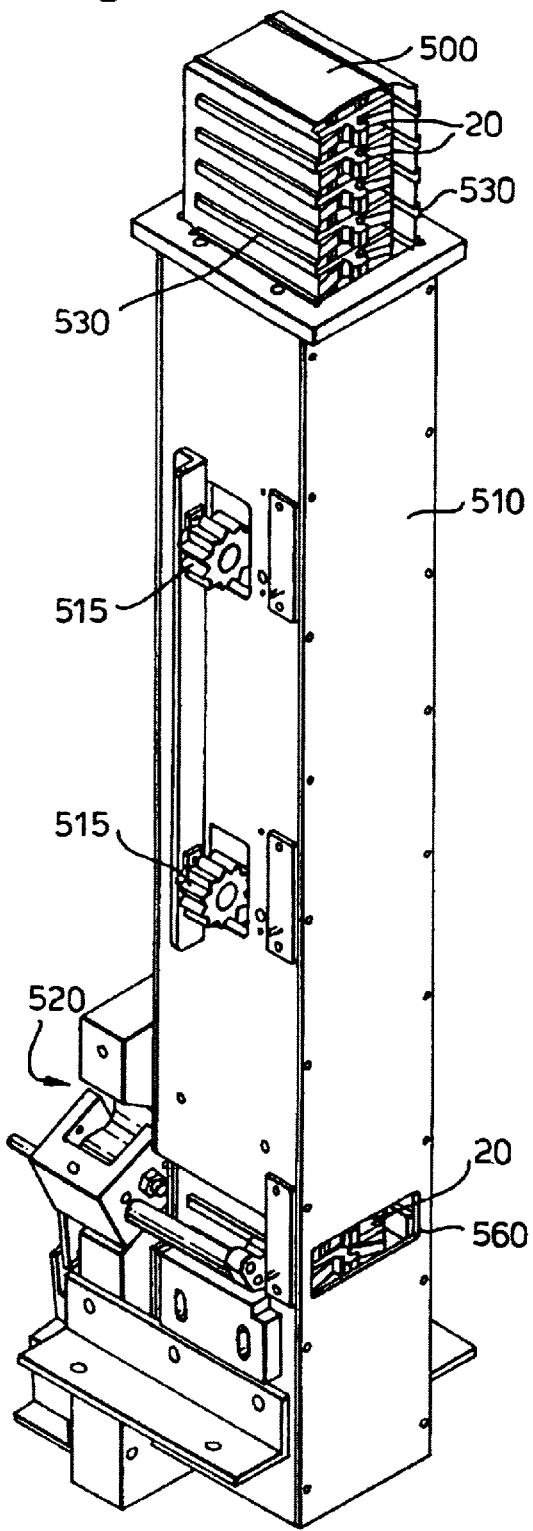
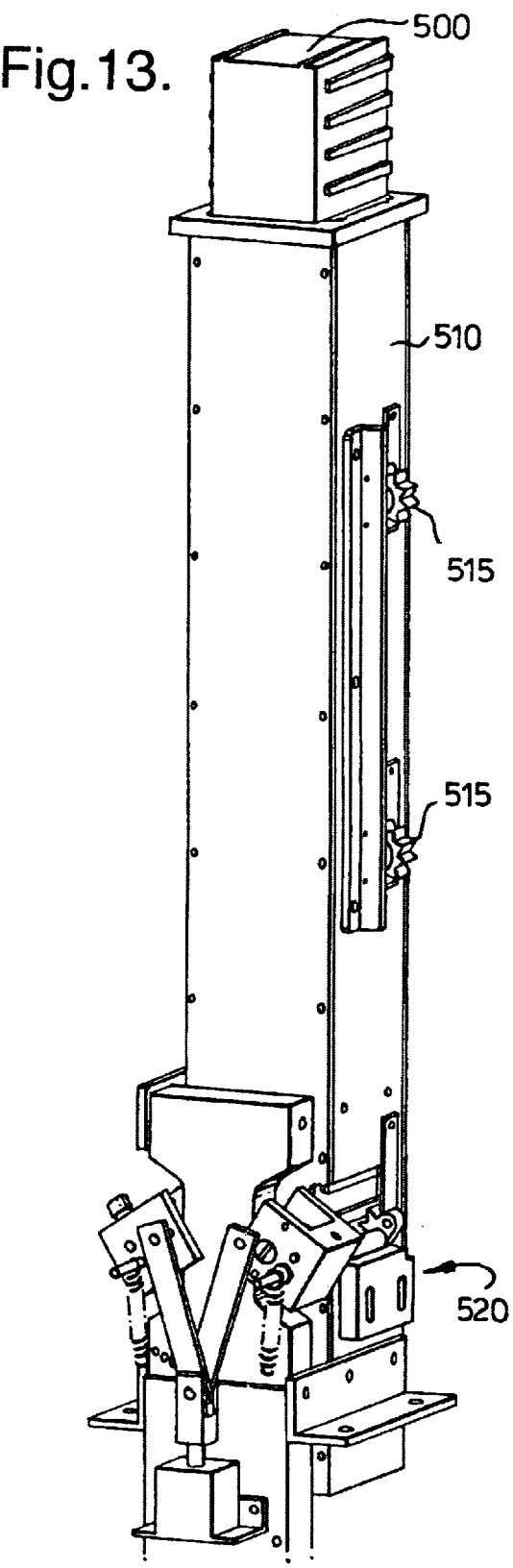

ASSAY DEVICE PROCESSING INSTRUMENT

FIELD OF THE INVENTION

The invention relates to an assay device processing instrument, for example for processing assay devices in the form of chips on which have been deposited an array of localised reactive sites containing different reactive species, for example different antibodies.

DESCRIPTION OF THE PRIOR ART

In this context, "assay" means the quantitative analysis of a substance to determine the proportion of some valuable or potent constituent e.g. the active constituent in a pharmaceutical.

An immunoassay is a technique which measures the presence of a substance (analyte) in a biological sample exploiting an immunological reaction between antibody and antigen.

In the fields of chemical/veterinary diagnosis or drug screening, it is necessary to analyse samples to determine the presence of certain analytes. Recently, it has been proposed to provide a set of different antibodies on respective reactive sites on a substrate such as a chip. The sample is deposited on the chip and following incubation and other processes, a chemiluminescence process is monitored to detect the presence or absence of the appropriate analyte at each site. This is described in more detail in EP-A-0902394.

The problem with analysis of such chips is that the processes are complex and require careful handling of the chips and thus significant manual intervention.

WO-A-93/23732 describes automatic staining apparatus for slide specimens but this is a histochemical process and has no relevance to assays.

SUMMARY OF THE INVENTION

In accordance with one aspect of the present invention, an assay device processing instrument comprises a plurality of assay device processing modules; a transport system including an assay device positioning assembly for transporting an assay device to each processing module, the assay device positioning assembly being adapted to transfer the assay device to each module to enable the assay device positioning assembly to transport another assay device while the transferred assay device(s) is processed; and a control system for controlling operation of the transport system such that each assay device is transferred between the modules in a predetermined sequence, and such that a number of assay devices can be processed in different modules simultaneously.

We have realised that it is possible to develop a sophisticated multi-tasking processing instrument by developing a transport system which can transport an assay device to a processing module and transfer the assay device to the module thus releasing the transport system to transport another assay device while the first is processed. Under computer control, a large number of assay devices could be processed simultaneously with such an instrument.

A variety of transport systems could be used. In one case a rotary transport system could be implemented which will be relatively compact. The simplest rotary system would involve a circular "shaft", and an assay device positioning assembly mounted for movement about the shaft, the shaft rotating until the positioning assembly is aligned with the respective processing module entry point for input or extraction of the storage units.

More complex options would involve rotating concentric assemblies/modules. The inner module could act as an incubator/shaker with the outer ring being the transport system. Thus, for example the incubator/shaker could shake with small angular movements about the vertical axis/shaft. The incubator/shaker could be multi-level/stack.

The storage units may be pushed out/pulled in between the inner incubator/shaker and the outer transport system via e.g. a push/pull motor assembly located within the centre of the inner incubator "ring".

In the preferred example, the transport system comprises a rail; an assay device positioning assembly mounted for movement along the rail; and a first motor responsive to the control system to move the assay device positioning assembly into alignment with the respective processing modules. Preferably, the rail is linear. This increases the simplicity and ease of design and modification of such a system over, for example, a rotary system.

In some cases, the transport system can be folded back on itself into a multi-plane system thus forming a more compact design than one which is based on a single plane.

In some cases, part of the transport system at each module could include means for transferring an assay device to and from the module. However, a simpler and preferred approach is to provide the transport system with a support movably mounted to the rail; an arm for engaging an assay device and movably mounted to the support for movement laterally relative to the rail; and a second motor on the support for causing lateral movement of the arm. In this case, the arm for moving the assay device moves with the support along the rail so that only a single such arm is required. Typically, the arm will move relative to the support substantially orthogonally to the rail although this is not essential.

Conveniently, the arm has means for gripping the assay device although in other cases, the arm could simply push the assay device to different positions or connect to it by other means such as a magnetic coupling.

Preferably, however, the assay device is supported in an assay device holder having a formation which cooperates releasably with the gripping means to enable the assay device to be positioned by the arm. Such an arrangement is described in more detail in EP Patent Application No. 98307732.2.

A variety of modules could be provided. Typically, they will include one or more of:

a) a buffer for storing more than one assay device or assay device holder;

b) an incubator;

c) a wash station; and, d) an assay device imaging station.

The use of a buffer is helpful in that it allows reactions to take place which require a period of time during which other assay devices can be transported and subjected to other processes. Conveniently, however, the buffer is provided by the incubator. Since assay devices normally have to be retained within the incubator for a period of time, this provides a useful dual purpose as a buffer.

An imaging station is needed in order to view the reaction sites after processing and it is important to restrict the access of ambient light. It is therefore necessary for the imaging station to be closed during the imaging process. This could be achieved by separately operating a door through which the assay device passes. This process can be simplified when the imaging station includes an entrance door which is automatically activated during transfer of the assay device to and from the imaging station.

This automatic activation could be achieved using sensors and the like to monitor movement of the assay device and a system responsive to the sensors to open the door. However, preferably the door is pivoted about an upper, horizontal axis to a wall of the imaging station and is coupled to a movable platform of the imaging station by a link pivoted to both the platform and the door whereby movement of the platform towards the door from either side of the door, causes the door to open and thereafter close once the platform has passed through from one side to the other.

As mentioned above, an important module for use during an immunoassay process is an incubator. In addition, it is usually necessary to shake or vibrate the assay device to promote the chemical reactions which are to take place.

Some examples of incubators are described in "Environmental Shakers/Incubators" by Shane Beck, Aug. 17, 1998. However, these are relatively unsophisticated.

In accordance with a second aspect of the present invention, an assay device incubator comprises a housing and a set of assay device supports positioned within the housing; means for independently heating each assay device within the housing; and means for shaking the support relative to the housing.

Unlike other systems, this new incubator enables shaking, incubation and accurate, independent heating control to be carried out at the same time so that no transfer is required between separate shaking and incubating modules during the reaction period.

Preferably, the frequency of the shaking means is variable while the stroke may be constant or variable. The stroke could be a simple to and fro horizontal motion, a vertical motion, an orbital motion or any combination of these. Typically, the type of motion will be chosen to optimize mixing procedures and speed of reaction. Additionally, periodic stops may be included in the shaking process to optimize reaction.

Although the transport system could be adjustable to load assay devices into appropriate locations within the incubator, when the supports are located in different vertical positions within a support unit, the support unit is preferably vertically movable to bring a selected support into alignment with the instrument transport system.

A further module which is used in an assay process such as an immunoassay process is a washing module. Conventionally, such modules include a probe for delivering wash fluid and an aspirator probe for removing wash fluid.

In accordance with a third aspect of the present invention, we provide an assay device washing module for washing an assay device located within an assay device well holder, the module comprising a wash fluid delivery probe and an aspirator probe mounted to a movable support, the aspirator probe being mounted at an angle to the vertical and the support being movable at substantially the same angle whereby when the aspirator probe is inserted into a well holder it is brought close to the side of the well holder.

This new washing module improves the aspiration of fluid from the well holder by directing the aspirator probe at an angle so that it is brought close to the side of the well holder and hence adjacent the channel which is formed between the assay device and the well holder. This then completely avoids any risk of contact with the active area and damage to the assay device while achieving significantly better aspiration since fluid is drawn from the channel around the assay device.

It is necessary to wash the probes between each assay device wash operation so preferably a probe wash region is located beneath the wash location of the well holder, the support being movable, in the absence of a well holder, to bring the aspirator probe into the wash region. This provides a convenient way of washing the probes while maintaining automatic operation of the washing module.

Preferably, the module further comprises a vacuum supply system coupled to the aspirator probe, the vacuum supply system including a vacuum vessel having a first port connected to a vacuum source, a second port connected to the aspirator probe and a third port connected to a drain via a drain pump.

BRIEF DESCRIPTION OF THE DRAWINGS

An example of an assay device processing instrument according to the invention will now be described with reference to the accompanying drawings, in which:

FIG. 2 is a perspective view of the main transport system;

FIG. 4 is a perspective view of an array of storage wells;

FIG. 8 is a block diagram of the wash system for the rack wash module shown in FIG. 7;

FIG. 10A is a perspective view of part of the imaging module;

FIG. 12 is a perspective view from one side of a stack loader;

FIG. 13 is a perspective view of the stack loader shown in FIG. 12 from a different side; and, FIG. 14 is an enlarged, perspective view of part of the stack loader shown in FIGS. 12 and 13.

DETAILED DESCRIPTION OF THE EMBODIMENT

Figure 1:
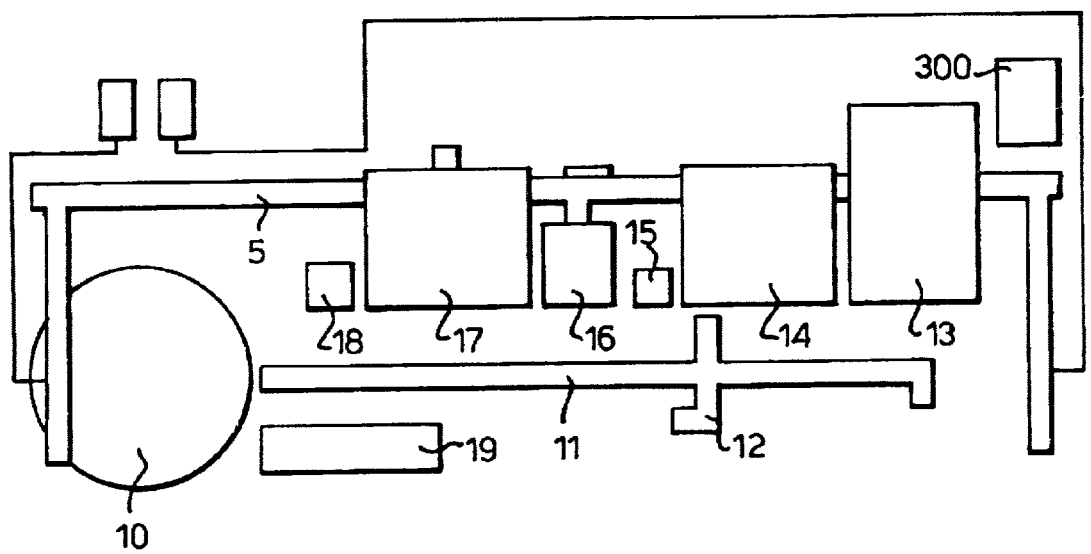
FIG. 1 is a block diagram of the instrument.

The immunoassay instrument shown in the drawings is designed to process assay device chips on which are deposited an array of localised reactive sites containing different antibodies. The chip is typically of ceramic or silicon. The chips are supplied "factory spotted" with an array of reactive species and for ease of handling are located in respective storage wells 1–3 (FIG. 4). Typically, the array of storage wells and chips is packaged for sending to a remote user. This is described in more detail in our co-pending European patent Application No. 98307732.2. For further ease of handling, the arrays of storage wells 1–3 are removably mounted in a carrying tray 20. This carrying tray (FIG. 5) is made of a plastics moulding and has two sets of crossbars 21,22 extending between opposite sidewalls 23,24 respectively. Raised ribs 21' assist in well positioning. Nine openings 25 are defined into which the respective storage wells can be located. The tray 20 has a flange projection 26 on one side and a protruding boss 27 on the opposite side and the purpose of these will be explained in more detail below. Each set of three storage wells 1–3 is loaded parallel to the crossbars 21 with the crossbars 22 entering between adjacent storage wells. The loaded carrier tray is then sealed in suitable packing materials for transportation. Preferably, the storage wells are left in place in the carrier tray and the tray used to move the storage wells about the immunoassay process. Alternatively, the storage wells can be supplied separately or removed from the carrier tray.

The user can decide whether to put one, two or three arrays of storage wells in the tray depending upon the number of samples to be tested.

FIG. 1 illustrates the main components of the instrument in block diagram form. The instrument comprises a sample tray 10 which holds a number of samples which are to be processed. This is provided adjacent one end of a main transport system 11 carrying a gripper arm module 12. As will be explained in more detail below, the gripper arm module 12 can be moved into alignment with a number of processing modules located alongside the main transport system 11. These modules include a rack entry module 13, an imaging module 14, a signal reagent module 15, a rack wash module 16, an incubator/shaker module 17, a preparation module 18, and a reagent store 19. In addition, a liquid handling system 5 is provided above the modules and main transport system.

Other modules may be included as necessary and one of the advantages of the instrument is that extra modules can be incorporated easily. For example, a small probe wash module is provided for the sampling arm and reagent arm.

The instrument is controlled by a microprocessor (300) linked with each of the modules and the main transport system 11 and with the liquid handling system 5.

Main Transport System 11

The main transport system 11 is shown in more detail in FIG. 2 and comprises an elongate rail 30 forming a slider on which is mounted the gripper arm module 12. A stepper motor 31, controlled by the microprocessor, is mounted at one end of the rail 30 and is coupled with a drive belt 32 which is entrained around an idler roller 33 at the other end of the rail 30. The belt 32 is secured to the underside of the gripper arm module 12. By forwarding suitable commands to the stepper motor 31, the belt 32 can be moved accurately to and fro to enable the gripper arm module 12 to be located opposite a selected one of the modules 10, 13–19. Although not shown, the belt 32 is preferably enclosed.

Figure 3A:
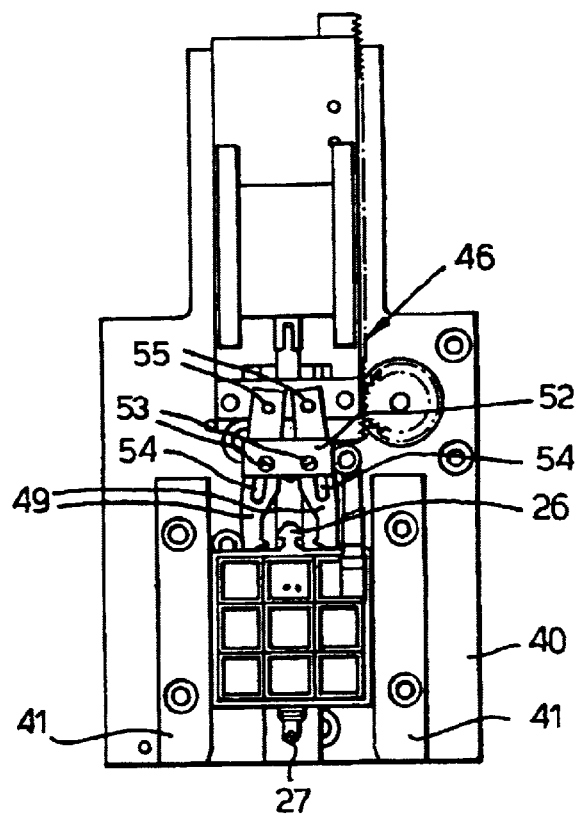
FIGS. 3A and 3B are a plan and perspective view respectively of the gripper arm module of the transport system.
Figure 3B:
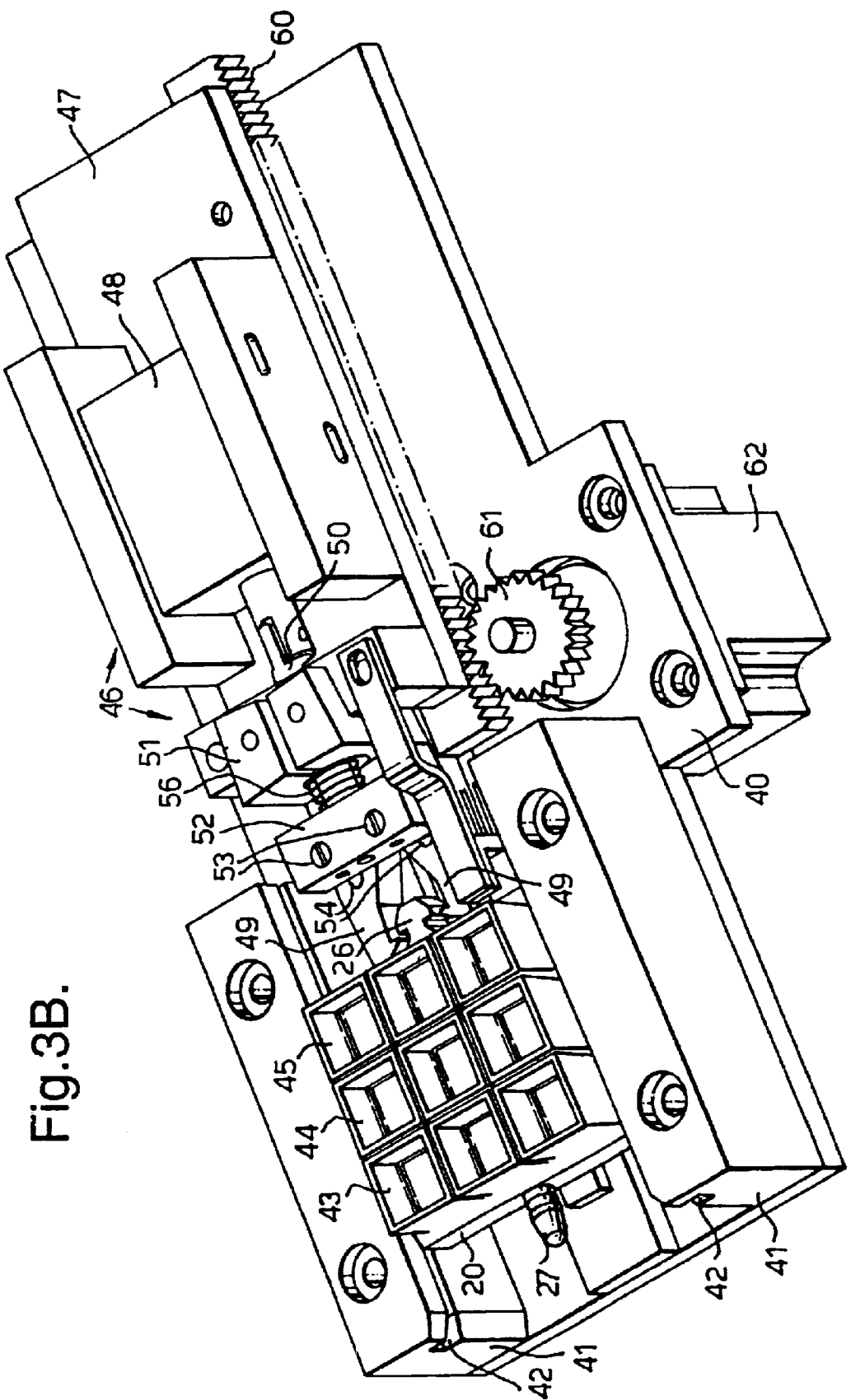
Figure 5:
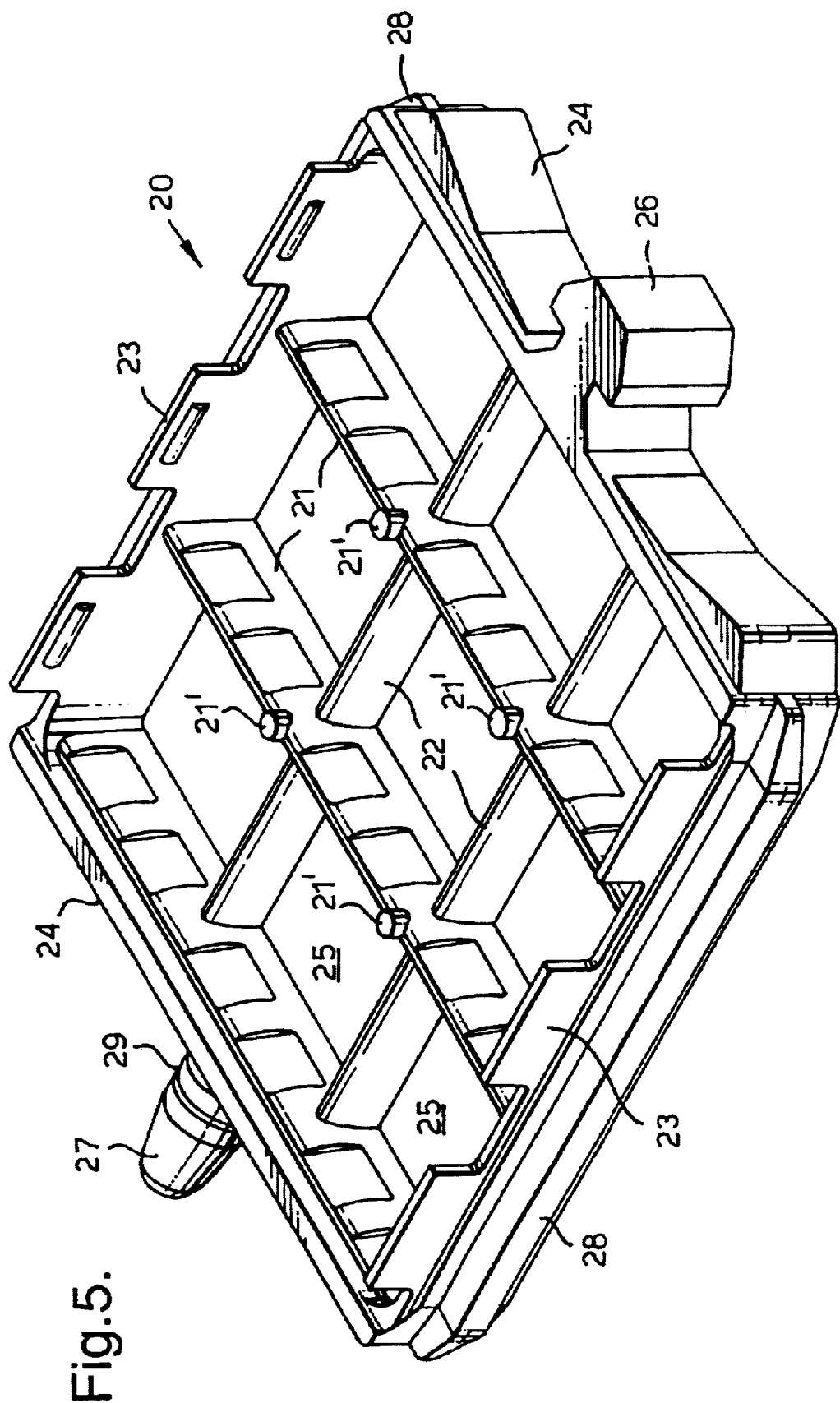
FIG. 5 is a perspective view of a carrying tray for the array of storage wells shown in FIG. 4.

The gripper arm module is shown in FIGS. 3A and 3B. The module comprises a platform 40 on which is mounted a pair of laterally spaced supports 41 having respective grooves 42 which are in alignment. These grooves are designed to receive slides 28 on opposite sides of the carrier tray 20 (FIG. 5). FIG. 3 illustrates such a tray 20 located in the gripper arm module. Three sets of storage wells 43–45 are mounted on the carrier tray 20.

A gripper arm assembly 46 is mounted for sliding movement on the platform 40 and comprises an auxiliary platform 47 to which solenoid 48 is secured. The solenoid 48 is connected to a pair of jaws 49 via an articulated rod assembly 50 which extends through a support housing 51 and terminates in a control block 52 having a pair of depending pins 53 which extend into slots 54 in the jaws 49. The jaws 49 are pivoted to the base 40 as shown at 55 in FIG. 3A.

The articulated rod assembly 50 is urged into an extended position as shown in FIG. 3B via a compression spring 56. Thus, the control block 52 is urged away from the solenoid 48 and in view of the cooperation between the pins 53 and the slots 54, this movement causes the jaws 49 to close about the flange projection 26 so as to hold the carrier tray 20 firmly on the gripper arm module. When the solenoid 48 is activated, the articulated rod assembly 50 retracts into the solenoid against the spring action, the corresponding movement of the block 52 relative to the jaws 49 causing the jaws to open thus releasing the carrier tray 20.

Movement of the gripper arm assembly 46 is controlled via a rack 60 and pinion 61, the pinion 61 being connected to a stepper motor 62 mounted on the underside of the platform 40. The stepper motor 62 is controlled by the microprocessor so as to move the carrier tray 20 to and from a module with which it is aligned.

Figure 11:
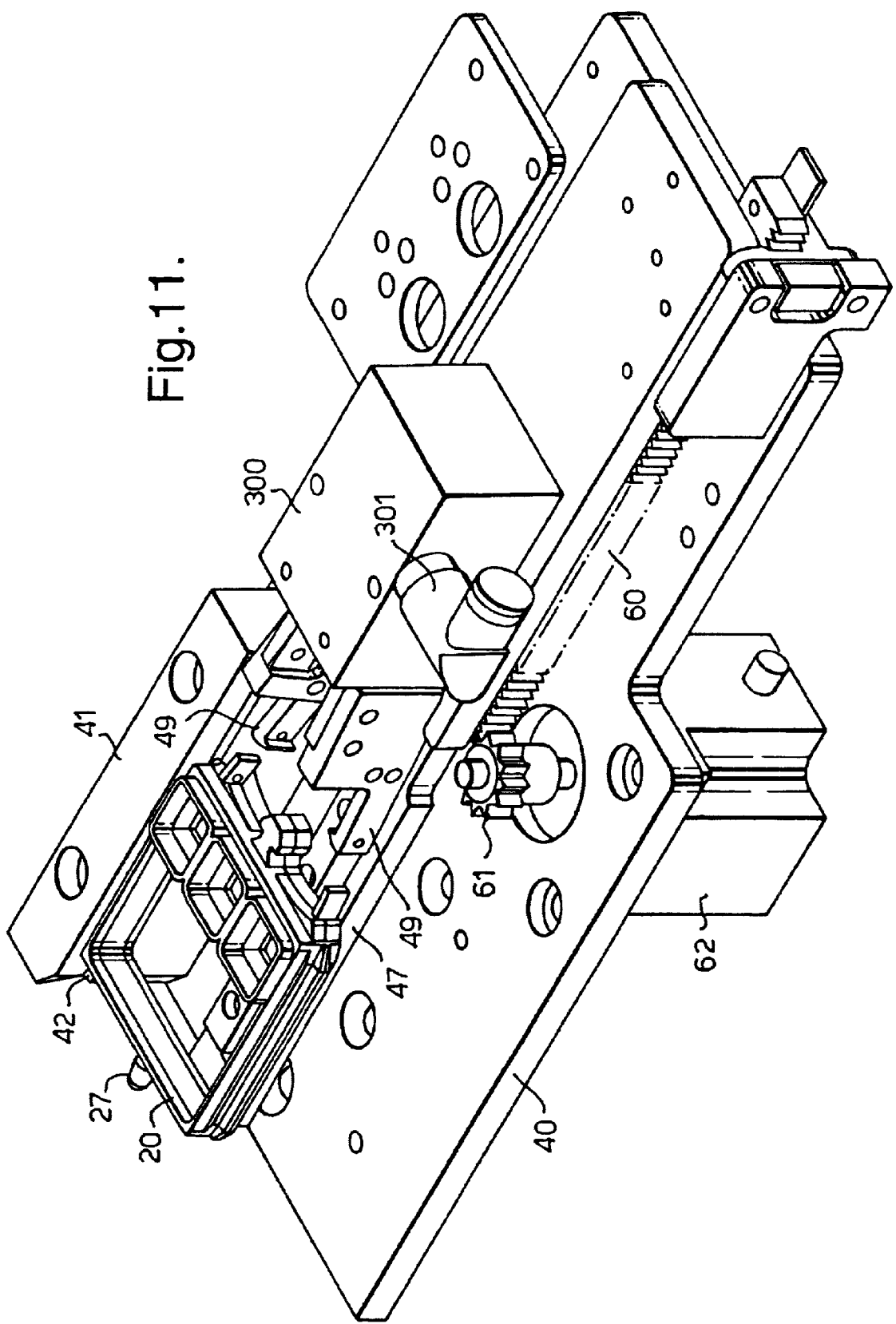
FIG. 11 is a view similar to FIG. 3B but of another example and with some parts omitted.

FIG. 11 illustrates an alternative form of the gripper arm assembly. In this Figure, the same reference numerals have been used as in FIG. 3B to illustrate similar components. The difference between the two gripper arm assemblies is that in FIG. 11, the jaws 49 are operated by a pneumatic module 300 supplied with air under pressure through an inlet port 301.

In passing, it should also be noted that pneumatic operation could be used in place of electrical operation for other modules within the instrument.

In a typical operation sequence, the gripper arm module 12 is moved on the main transport system rail 11 opposite the desired module. The motor 62 is then actuated to move the plate 47 and the carrier tray 20 bodily to the left as shown in FIG. 3B, the tray 20 transferring from the grooves 42 into corresponding grooves provided in the receiving module. The carrier tray 20 will then be held by engagement between the boss 27 and a Bal seal mounted at the rear end of the support surface. This Bal seal is a circular spring which locates in a circular groove 29 (FIG. 5) at the rear of the boss 27. The advantage of this arrangement is that the Bal seal can hold the carrier tray 20 relatively securely but will readily release the carrier tray when it is pulled by the jaws 49. However, alternative methods for holding the carrier tray are also envisaged including magnetic catches and the like.

Once the boss 27 is securely received in the corresponding Bal seal (which may be determined by a microswitch and/or following a certain predetermined number of steps by the stepper motor 62), the solenoid 42 is actuated to release the jaws 49 and the motor 62 is then actuated in the opposite direction to retract the jaw assembly.

Initially, the racks supported in the respective carrier trays 20 must be fed into the instrument and this can be achieved in any conventional manner. In one method, the racks (or storage well arrays) and carrier trays are prepackaged and supplied on reels to enable a range of different assays to be undertaken. The reel is mounted in the rack entry module 13 where the tray and storage wells can be unwrapped and supplied onto the platform 40 of the gripper arm module 12 which is suitably positioned adjacent the rack entry module.

Figure 14:
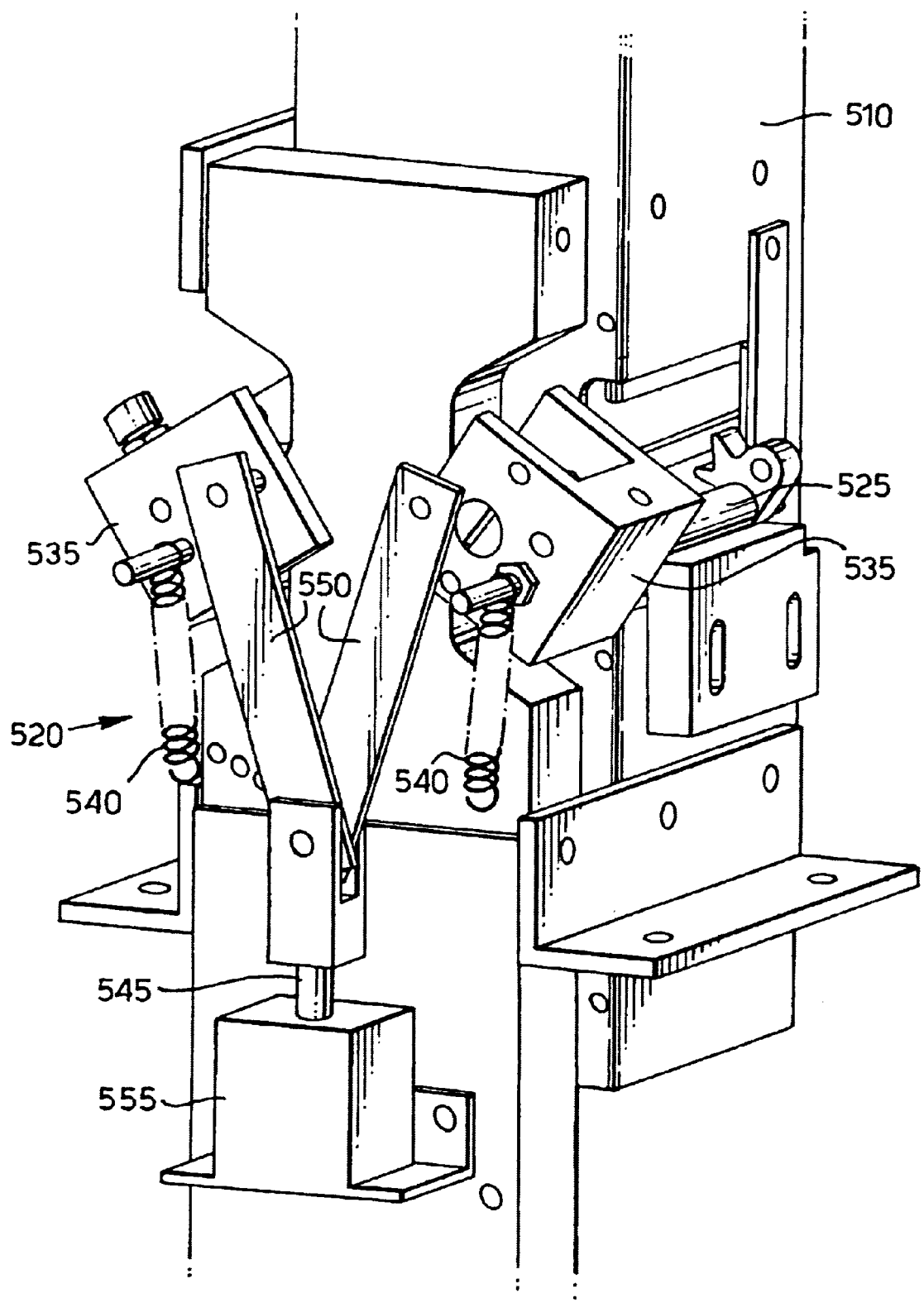

FIGS. 12–14 illustrate a preferred form of stack loader to constitute the rack entry module 13. In this case, a stack of trays 20 is loaded into a carrier 500 which is dropped down into the top of a "chimney" 510 of the stack loader. A pair of toothed gear wheels 515 on the side of the stack loader chimney 510 act to slow down the stack as it falls under gravity by engaging opposed pairs of rungs 530 on the side of the carrier. The falling stack stops on meeting a prior loaded stack or, if the stack loader is empty, on meeting an incrementing mechanism 520.

The incrementing mechanism 520 is shown in more detail in FIG. 14. The mechanism comprises a pair of single toothed arms 525 (only one visible in FIG. 14) which engage oppositely placed rungs 530 on the carrier 500. The arms 525 are coupled to pivot blocks 535 which are urged to the position shown in FIG. 14 by respective compression springs 540. Movement of the blocks is caused by a pneumatic actuator 555 connected to a pneumatically operated piston 545 coupled via connecting arms 550 to each block 535.

When the pneumatic actuator 555 is momentarily actuated, the rod 545 moves upwards causing corresponding pivotal movement of the blocks 535 and the arms 525 thus releasing the teeth on the arms 525 from the corresponding rungs 530 which allows the carrier to drop down. Since this release is only momentary, the arms 525 immediately pivot back to their holding position under the influence of the springs 540 so that the next rungs 530 engage the teeth.

When the carrier 500 is held by the toothed arms 525, a carrying tray 20 is aligned with an outlet opening 560.

In some cases, more than one stack holding device could be used. Furthermore, a linear feeding system (not shown) could be provided to feed a number of stacks in a slightly downward sloping track to the top of the stack holding device.

Samples under test are manually loaded into a standard commercial sample tray 10 which will accept a variety of different sample tubes and cups. (Instead, a rack or other loading system (not shown) could be used.) The instrument is then activated and the gripper arm module 12 moves to the preparation station 18. The liquid handling system 5 is then programmed to extract a portion of each liquid sample from the tray 10 and to add this to one chip/well positioned on the carrier 20 at the preparation station 18. Further portions will be extracted from the same or another sample and added to further wells in turn until all three racks of storage wells or the required number of storage wells are filled. The gripper arm module 12 is then moved to the reagent store 19 and portions of reagents from that module are extracted by the liquid handling system and added to each storage well. The carrier 20 and storage wells are then moved by the main transport system 11 to the incubator/shaker module 17.

Incubator/Shaker Module 17

Unlike a conventional incubator, this module, shown in more detail in FIG. 6, also shakes the carrier tray and storage wells to promote the chemical reactions taking place. In addition, it acts as a buffer since it can hold more than one carrier tray.

The incubator/shaker module 17 comprises a support unit 70 defining a set of separate compartments or bays 71 (sixteen in this example arranged in two columns of eight). Each compartment 71 has a pair of grooves 76 into which a carrier tray 20 can be slid by the gripper arm module 12. In addition, each compartment has a heating element and temperature control sensor 72 located above the grooves 76.

Typically, the temperature of each bay 71 and associated assay device (containing reagents and biochip) is controlled independently via a microprocessor (not shown) and may be set at 37° C. for immunoassay applications. However, the temperature of each compartment 71 can be adjusted separately, if desired. Temperatures from room temperature to above 70° C. may be used. Even higher temperatures are obtainable with appropriate assay device, heater, sensor and other incubator components/materials. Specific temperature/time profiles can be applied to suit particular assay processing requirements e.g. the temperature ramped up quickly to 70°.

In the present design, the compartments 71 are open at one end. Even tighter and more uniform temperature control can be maintained within the compartments 71 and across the assay device by providing each compartment with an individual or common/shared door (not shown). The door(s) open and close to allow insertion/removal of the assay device. The doors or door limit air flow and heat loss to the rest of the instrument thereby reducing the heat input required. (Heat generation within the instrument is also minimised.) Construction of the compartment and doors from insulating materials also reduces heat loss and heat input requirements.

An alternative to individual doors and a potentially mechanically simpler option is to provide a fixed insulating wall in front of and close to the open compartments of the moveable incubator/shaker unit. Access to the individual compartments is achieved via a single door through the wall per column of compartments. The door or doors in this insulating wall are located adjacent the main transport axis and individually open/close to allow positioning of the assay device in the adjacent incubator columns.

Another approach (not shown) involves the complete enclosure of the existing incubator/shaker within a larger temperature controlled chamber. The temperature of the outer chamber would be maintained by a hot air generator at a value slightly lower the required lowest incubator compartment temperature. Small additional heat input from the individual heating elements in each compartment allows the temperature of the individual compartments to be even more tightly controlled.

The unit 70 is supported via flange members 73 on respective supports 77 secured to the main housing 200 and is guided for vertical movement by a pair of vertically extending rods 74 passing through apertures 201 in the flange members 73. This enables any one of the vertically spaced compartments 71 to be located in alignment with the gripper arm module 12. The rear of each compartment 71 is provided with a Bal seal 202 previously described so that when a carrier tray 20 is slid into the grooves 76, the boss 27 engages and is held by the Bal seal.

Vertical movement of the unit 70 is caused by a stepper motor 75 linked to one of the supports 77 via a screw threaded rod 79 linked to the support. The stepper motor 75 is controlled by the microprocessor.

Figure 6B:
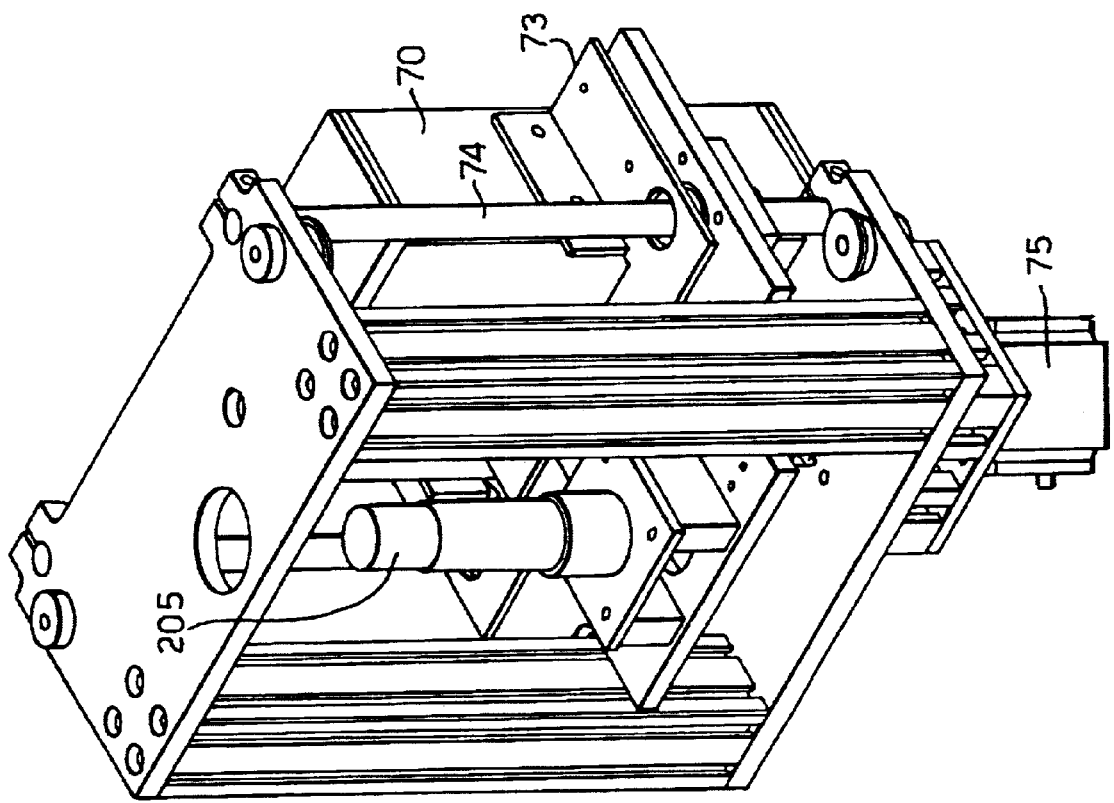
FIGS. 6A–6D are a side elevation, a perspective view from above, one side and the rear, a perspective view from above, front and the one side, and a perspective view from above, front and the other side respectively of the incubator/shaker module.
Figure 6A:
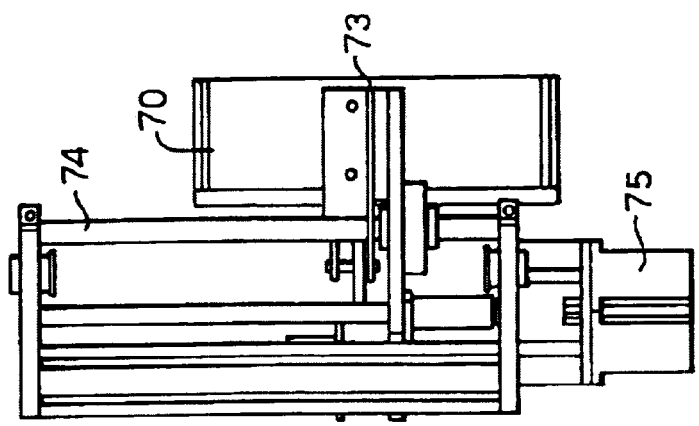
Figure 6C:
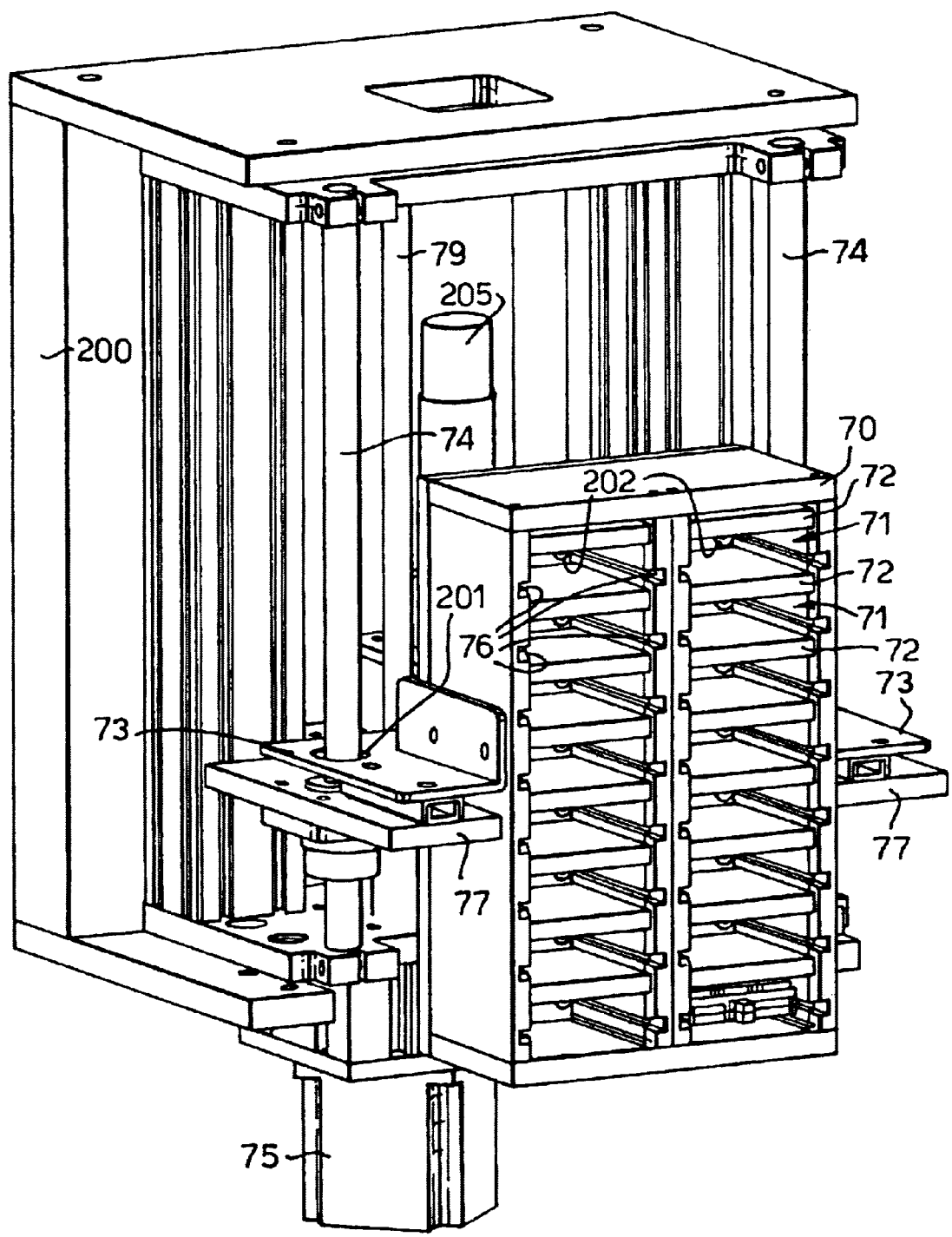
Figure 6D:
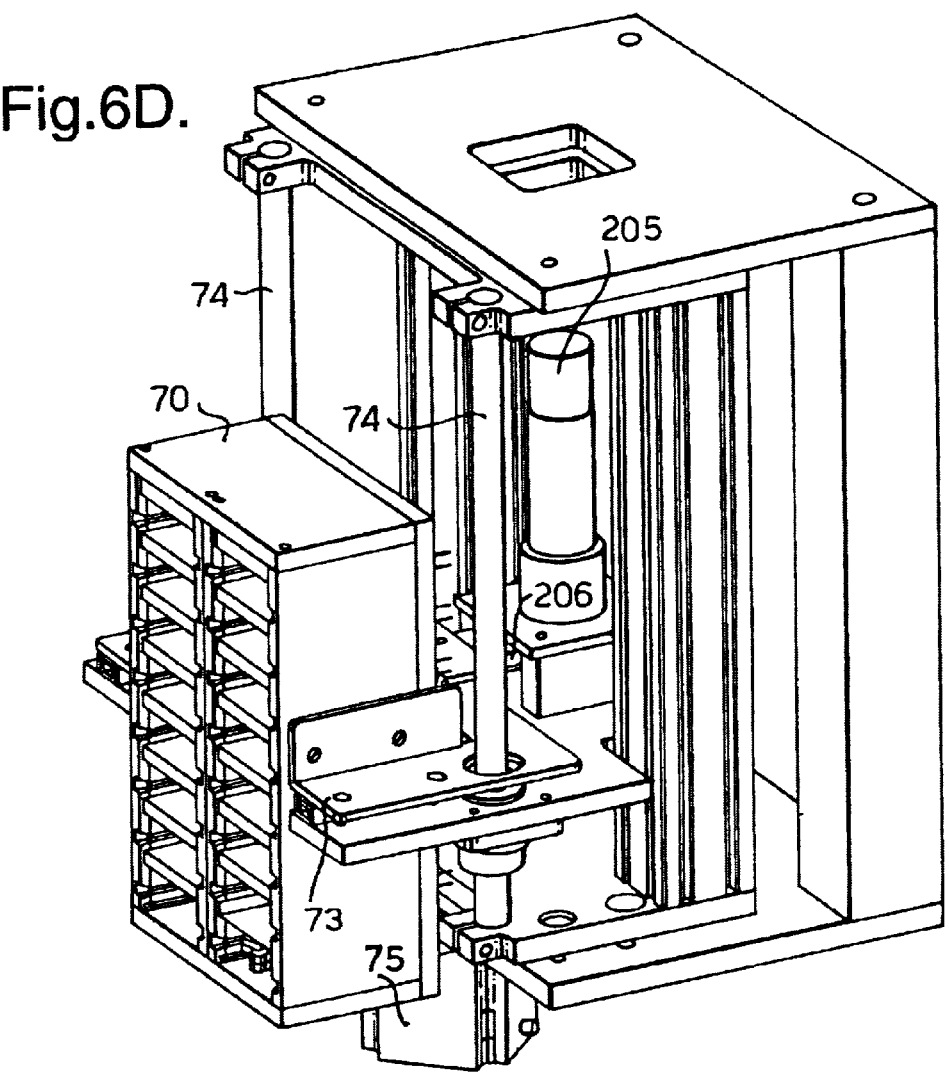
Figure 6E:
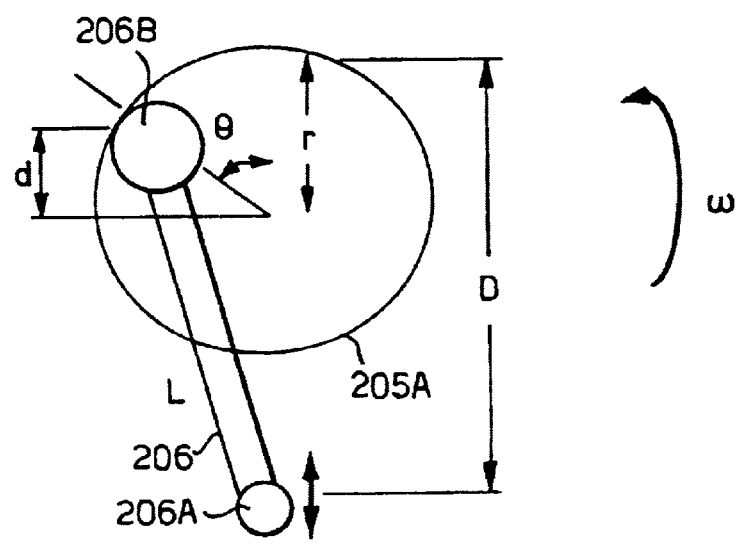
FIG. 6E is a schematic view of the shaker arrangement.

In addition to the vertical movement described to enable the unit 70 to be aligned with the gripper arm module 12, the incubator can also cause horizontal shaking movement of the unit 70. Thus, it will be noted that the unit 70 is loosely mounted about the support rods 74 via the flange members 73, those flange members 73 sliding on the supports 77. This means that the unit 70 can be shaken to and fro in a horizontal direction by causing sliding movement of the flange members 73 over the support members 77. This shaking movement is caused by operating a motor 205 which rotates a shaft 205A (FIG. 6E). A connecting arm 206 is connected at one end 206A to the incubator and at the other end 206B via a drive pin to a point on the shaft 205A offset from its axis of rotation.

Alternative designs may use a vertical, an orbital, or a horizontal motion or a combination of any of these motions.

The frequency, amplitude (stroke) and "operating profile" of the shaking mechanism will be selected following assay performance studies in which the frequency and amplitude are varied and also the shaker mode (linear, orbital and rotary and combinations) compared.

In a simple case, the incubator undergoes a simple cosine wave linear motion in accordance with the relationship:

Displacement of incubator $D=\sqrt{(L^2-r^2\sin^2\theta)}+(r-r\cos\theta)$ where θ is the angular position of the point 206 $\theta=2\pi\omega t$ ω is the shaker and drive motor frequency (cycles per second)

t is time (seconds)

L is the length of the connecting rod d=r cos θ is the displacement of the drive pin.

The stroke of the shaker may be changed by varying the drive pin offset with respect to the motor shaft.

The operating profile can also take the form of programmable on/off sequence, with a fixed frequency and stroke, e.g. 5 minutes on and 1 minute off.

For the linear as well as the other shaking techniques, the optimum shaking frequency and amplitude are influenced especially by factors affecting fluid motion within the storage well, e.g. the assay well dimensions, the profile of the well walls, and volume (depth) of liquid and also the physical properties of the liquid and well material.

The incubator will, of course, be housed in a generally closed housing (not shown).

The shaker frequency pattern can be changed although typically the stroke will be preset. A typical stroke is in the order of 2 mm with frequencies in the order of 1–20 cycles per second.

It will be appreciated that by combining the incubator and shaker, a reduction in the processing time is obtained over the previous need for separate modules, while enabling more than one carrier tray to be provided in the incubator at one time provides a useful buffer capability. In particular, it will be noted that as with the other modules, once the carrier tray has been transferred to the incubator module 17, the main transport system 11 is free to handle another carrier tray and storage wells thus allowing the instrument to maximise the number of wells being processed at any one time.

After an appropriate interval for analytes to bind to the reactive species (typically about 30 minutes), the carrier tray 20 is retrieved by the gripper arm module 12 and moved to the rack wash module 16.

Rack Wash Module 16

Figure 7:
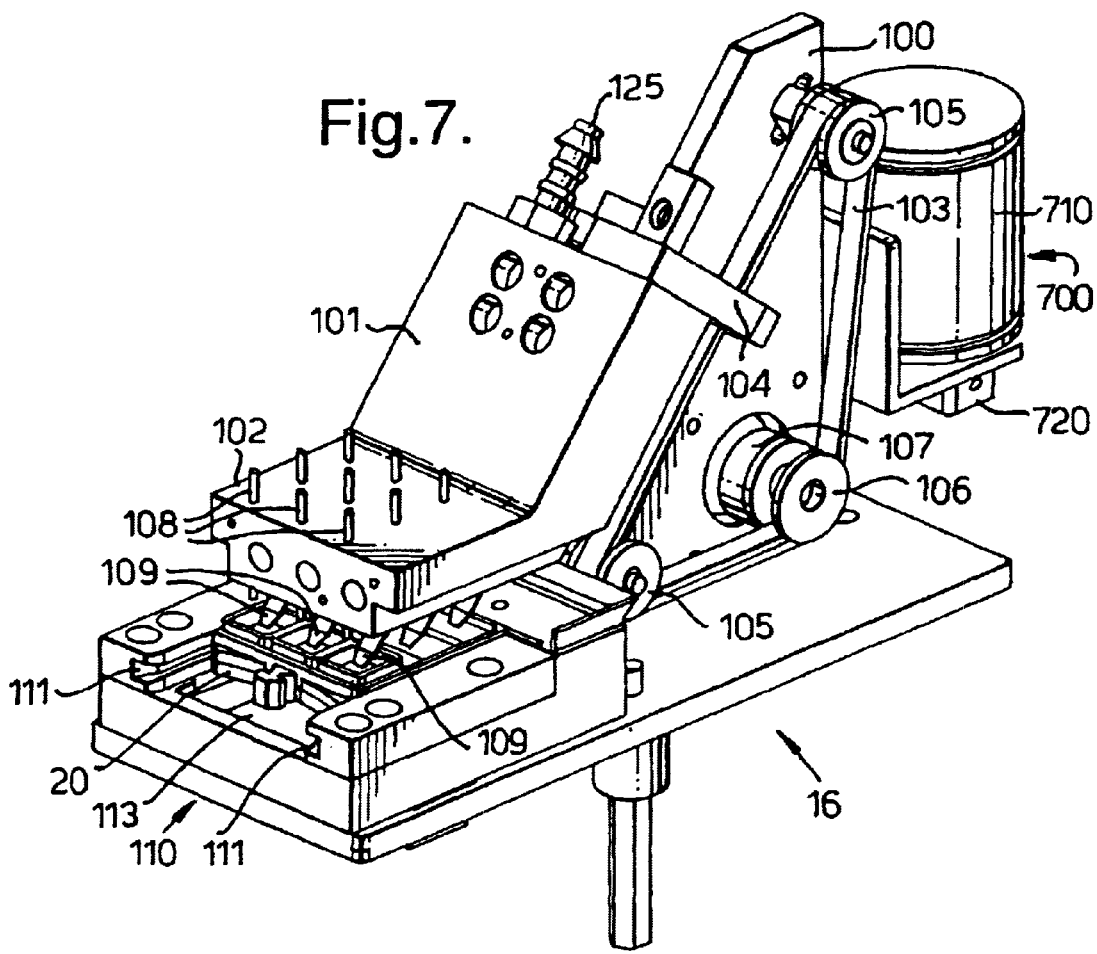
FIG. 7 is a perspective view of the rack wash module with some parts omitted for clarity.

The rack wash module 16 is shown in FIG. 7 and in schematic form in FIG. 8. The module comprises a generally triangularly shaped support block 100 on which is slidably mounted a member 101 having, at its lower end, a horizontally extending portion 102. The position of the member 101 along the support block 100 is controlled by a belt 103 to which the member 101 is secured at 104, the belt being entrained around idler rollers 105 and a drive roller 106 mounted to the support block 100. The drive roller 106 is controlled by a stepper motor 107, also mounted to the support block 100, and controlled by the microprocessor.

The horizontal portion 102 of the member 101 supports nine vertically oriented wash delivery jets 108 and nine angled aspirator jets 109, only some of which can be seen in the drawings.

A carrier tray support housing 110 is mounted in front of the support block 100 and has a pair of grooves 111 which receive the slides 28 of a carrier tray 20. In this case, the Bal seal 112 can be seen in FIG. 7 located at the rear of the carrier tray support assembly 110. A probe wash reservoir 113 is located below the location of a carrier tray.

In use, the gripper arm module 12 delivers a carrier tray 20 to the support assembly 110 with the slides 28 of the tray being received in the grooves 111. The carrier tray is pushed forward until the groove 29 of the boss 27 is engaged by a Bal seal (not shown). The gripper arm module 12 then retracts leaving the carrier tray in place. At this time, the member 101 is in its retracted position shown in FIG. 7.

The stepper motor 107 is activated to slide the member 101 downwardly causing the aspirator jets 109 to enter respective storage wells 1–3 until they almost touch the chips located in the storage wells. In practice, the aspirator jets 109 are angled in such a way that they approach very closely to a channel which is formed between the edge of the chip and the side wall of the storage well.

A conventional washing process is then carried out under the control of the microprocessor which is coupled with various valves and pumps to be described in connection with FIG. 8. It should be noted that the valves allow individual control of wash delivery via the shorter vertical jets to each rack of three storage wells and in connection with the jets 108, their position over each well is not critical. The longer, angled aspirator jets 109 aspirate from a point close (for example 100–200 μm) to the edge of the chip, base and side wall of the well achieving a high degree of liquid removal. However, there is no contact with the active area so that there is no risk of damage to the chips.

In the preferred arrangement, the module includes a shaker system 700 to shake the rack during washing. The shaker system comprises a shaker motor 710 and an offset mass 720. The shaking/vibration motion is currently small compared to the motion of the incubator/shaker. Typically, the drive motor 710 rotates at 50 Hz though the frequency and mass may be adjusted to optimize rack wash effectiveness. Other vibrating means could be employed for rack wash shaking/vibration e.g. ultrasonics or moving coil (loudspeaker).

Upon completion of the rack wash process, the stepper motor 107 is activated to retract the member 101 so that the gripper arm module 12 can extract the carrier tray 20. Following extraction of the carrier tray 20, the stepper motor 107 is again activated to lower the member 101 to a much lower position in which the aspirator jets 109 enter the reservoir 113 for cleaning in order to avoid contamination of subsequent samples and assay procedures. An important aspect of this is that the jets are washed using a different liquid, for example clean water, from that supplied to the jets 108. This prevents crystallisation from the wash fluid on the probes which can occur with known systems.

As can be seen in FIG. 8, the probes or jets 108 are connected in groups of three to respective pumps 120 (only one shown) which in turn are connected to a wash buffer reservoir 121 via respective valves 122. Operation of the valves 122 supplies a mixture of water from a reservoir 123 and wash solution to the respective pump 120 and hence to the corresponding three jets 108. The reservoir 123 is also connected via a pump 124 controlled by the microprocessor to deliver clean water to the reservoir 113. The aspirator jets 109 are connected to a nozzle 125 which in turn is connected via a vacuum vessel 126, a vacuum tank 128, and a vacuum control valve 127 to a vacuum pump 129 which is operated during aspiration. Fluid which has been aspirated is collected in the vacuum vessel 126 and is drained off via a continuously running pump 130 to a drain 131. The drain 131 is also connected to an outlet 132 from the reservoir 113.

An important aspect of the system shown in FIG. 8 is the use of a double chamber arrangement to ensure that liquid aspirated from the storage wells is trapped in the smaller vacuum vessel 126 and does not reach the main vacuum tank 128 or vacuum pump 129. The use of the main vacuum tank 128 and the vacuum control valve 127 along with the vacuum pump 129 allows a higher "suction impulse" than could be achieved with a simple pump alone.

The system operates as follows. Operation of the pump 129 is controlled by a microprocessor. Upon starting the vacuum pump, pressure is reduced in the smaller vacuum vessel 126 and liquid is aspirated from the storage wells into the vacuum vessel 126.

Alternatively, individual or groups of storage wells may be aspirated in turn by replacement of the single vacuum control valve 127 by multiple valves linked to specific aspiration jets thereby achieving a further increase in "suction impulse".

Following rack washing, the carrier 20 is then transported by the main transport system 11 to the signal reagent module 15 or back to the preparation module 18 dependent on whether the assay is competitive or sandwich based respectively. For competitive assays, conjugates are added to the storage wells directly on visiting the preparation module 18 whereas for sandwich based assays a diluent assay buffer is added first, incubated and then washed before conjugates are added, further incubated and washed.

The carrier 20 is then transported by the main transport system 11 to the imaging module 14. In a preferred approach, however, a cover is placed over the storage wells before they leave the signal reagent module 15 or the preparation station 18 to prevent light from entering the storage wells. This cover may then be removed prior to transport to, or within, the imaging module.

Figure 9:
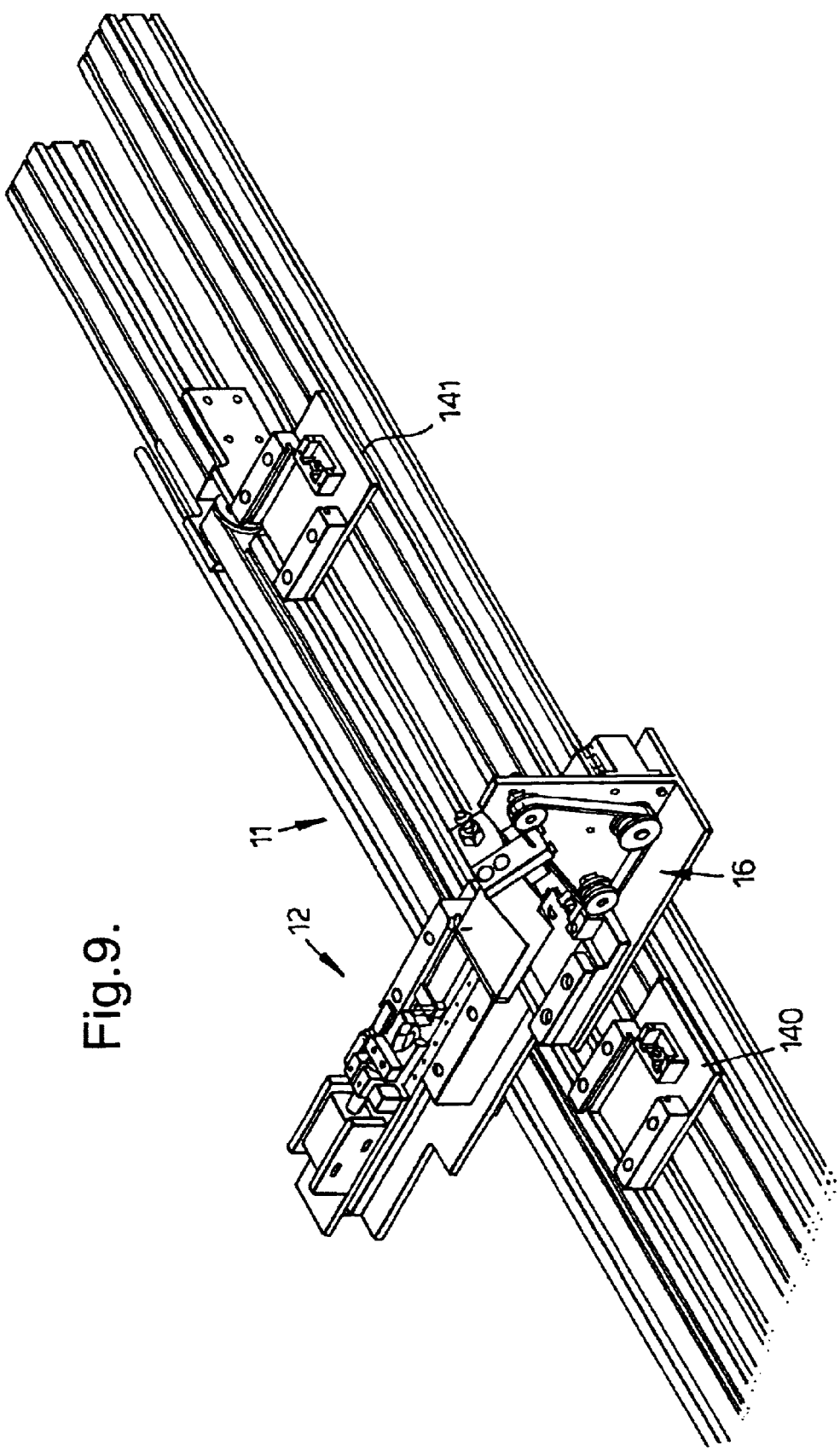
FIG. 9 illustrates the relative locations between the rack wash module and the main transport system in perspective view.

FIG. 9 illustrates the main transport system and the rack wash module 16 with the gripper arm module 12 positioned to supply a carrier tray to the rack wash module. FIG. 9 also illustrates the carrier tray supports 140,141 of two other modules which are otherwise not shown.

Imaging Module 14

The imaging module 14 has a generally conventional form for monitoring chemiluminescence and will not be described in detail. However, the manner in which the carrier tray is delivered to and retrieved from the imaging module, to assist automatic operation, will be described with reference to FIGS. 10A and 10B.

Since it is necessary for the imaging module 14 to be light tight, in the present example, a door 150 is provided at the entrance to the imaging module 14 which can be automatically actuated upon delivery and retrieval of a carrier tray.

Figure 10B:
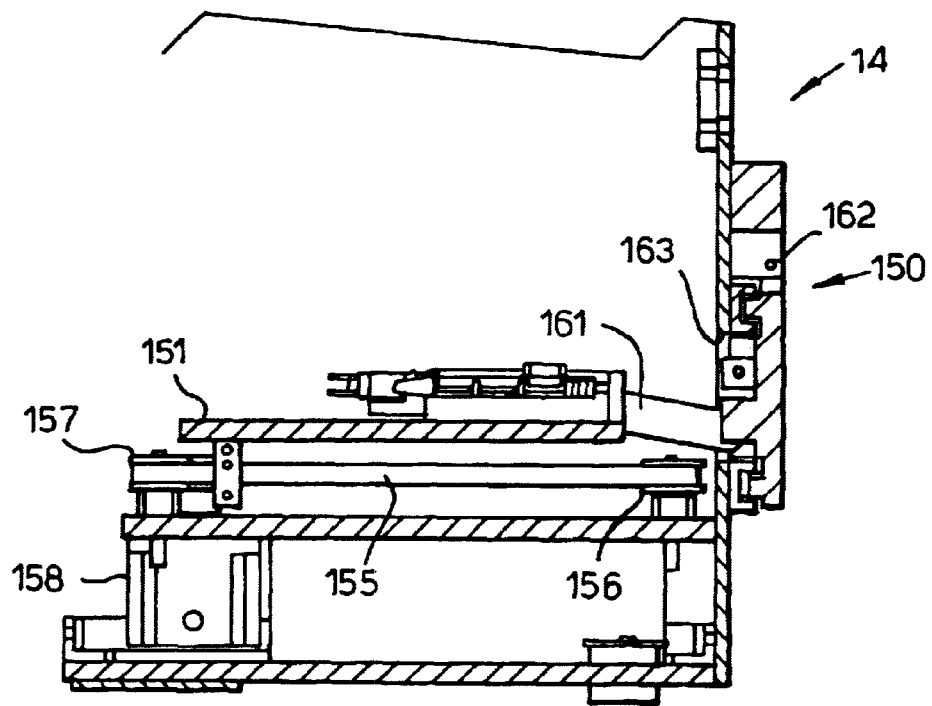
FIG. 10B is a cross-section through the components shown in FIG. 10A.

The imaging module 14 includes a carrier tray support 151 which is shown in both FIGS. 10A and 10B located within the imaging module. The carrier tray support 151 includes a pair of blocks 152 defining facing grooves 153 in which the carrier tray slides 28 are received. A block 154 carries a Bal seal (not shown).

The carrier tray support 151 is slidably mounted in the imaging module for movement between the position shown in the drawings to an equivalent position on the other side of the door 150 in which it can be aligned with the gripper arm module 12. Movement of the carrier tray support 151 can be controlled by a belt 155 entrained around an idler roller 156 and a drive roller 157 driven by a stepper motor 158 under the control of the microprocessor.

A microswitch on the front left of the carrier support tray is used to switch off the drive voltage to an optical emitter detector adjacent the ball seal in order to eliminate light emission during the imaging process.

The end of the carrier tray support 151 adjacent the door 150 carries a link 161 pivoted to one of the blocks 152 and to the door 150.

When the carrier tray support 151 is moved towards the door 150 (to the right in FIG. 10B) by operation of the stepper motor 158, the link 161 will push the door 150 in an anti-clockwise direction about a hinge 162 thereby opening an aperture 163 so that the carrier tray support 151 together with the carrier tray can be moved through the aperture 163 towards the gripper arm module 12. This movement will cause the link 161 to pivot in an anti-clockwise direction about its pivot connection to the block 152 so that as the carrier tray support 151 moves through the aperture 163, the links 161 will continue to pivot in the anti-clockwise direction allowing the door 150 to close behind it. It will be appreciated that a similar process will operate when the carrier tray support 151 is returned into the imaging module 14.

The imaging process carried out within the imaging station will have a conventional form or may be described in EP-A-0902394.

Once the imaging process has been completed, the carrier tray 20 moved back through the aperture 163 by the motor 158 and is extracted by the gripper arm module 12. The carrier tray can then be taken to a waste disposal location (not shown) for dumping.

We claim:

1. An assay device processing instrument comprising:

a plurality of different assay device processing modules, each module having an opening for receiving an assay device;

a transport system including an assay device positioning assembly for transporting an assay device to each different processing module, the assay device positioning assembly being adapted to transfer the assay device into each different processing module via the opening to enable the assay device positioning assembly to transport another assay device to another processing module while the transferred assay device(s) is processed; and a control system for controlling operation of the transport system such that each assay device is transferred between the different processing modules in a predetermined sequence, and such that a number of assay devices can be processed in different processing modules simultaneously, the transport system further comprises a rail; the assay device positioning assembly mounted for movement along the rail; and a first motor responsive to the control system to move the assay device positioning assembly into alignment with the respective processing modules, the transport system further comprises a support movably mounted to the rail; an arm for engaging the assay device and movably mounted to the support for movement laterally relative to the rail; and a second motor on the support for causing lateral movement of the arm, wherein the second motor is coupled to the arm by a rack and pinion arrangement.

2. An assay device processing instrument comprising:
- a plurality of different assay device processing modules, each module having an opening for receiving an assay device;
- a transport system including an assay device positioning assembly for transporting an assay device to each different processing module, the assay device positioning assembly being adapted to transfer the assay device into each different processing module via the opening to enable the assay device positioning assembly to transport another assay device to another processing module while the transferred assay device(s) is processed; and
- a control system for controlling operation of the transport system such that each assay device is transferred between the different processing modules in a predetermined sequence, and such that a number of assay devices can be processed in different processing modules simultaneously,
  - the transport system further comprises a rail; the assay device positioning assembly mounted for movement along the rail; and a first motor responsive to the control system to move the assay device positioning assembly into alignment with the respective processing modules,
  - the transport system further comprises a support movably mounted to the rail; an arm for engaging the assay device and movably mounted to the support for movement laterally relative to the rail; and a second motor on the support for causing lateral movement of the arm, wherein the arm is spring loaded and urged towards its retracted position.

3. An assay device processing instrument comprising:
- a plurality of different assay device processing modules, each module having an opening for receiving an assay device;
- a transport system including an assay device positioning assembly for transporting an assay device to each different processing module, the assay device positioning assembly being adapted to transfer the assay device into each different processing module via the opening to enable the assay device positioning assembly to transport another assay device to another processing module while the transferred assay device(s) is processed; and
- a control system for controlling operation of the transport system such that each assay device is transferred between the different processing modules in a predetermined sequence, and such that a number of assay devices can be processed in different processing modules simultaneously,
  - wherein the modules include one or more of:
    - a) a buffer for storing more than one assay device or assay device holder;
    - b) an incubator;
    - c) a wash station; and
    - d) an assay device imaging station, wherein the assay device imaging station module includes an entrance door which is automatically activated during transfer of the assay device to and from the assay device imaging station.

4. An instrument according to claim 3, wherein the door of the assay device imaging station module is pivoted about an upper, horizontal axis of a wall of the imaging station and is coupled to a movable platform of the assay device imaging station by a link pivotable relative to both the movable platform and the door whereby movement of the movable platform towards the door causes the door to open and close.

5. An instrument according to claim 4, wherein the movable platform is positioned to receive an assay device located outside the door and adjacent the transport system.

6. An instrument according to claim 4, wherein the movable platform is moved by a third motor coupled to the control system.

7. An instrument according to claim 4, wherein the door forms a light tight closure with the assay device imaging station module wall.

8. An assay device processing instrument comprising:
- a plurality of different assay device processing modules, each module having an opening for receiving an assay device;
- a transport system including an assay device positioning assembly for transporting an assay device to each different processing module, the assay device positioning assembly being adapted to transfer the assay device into each different processing module via the opening to enable the assay device positioning assembly to transport another assay device to another processing module while the transferred assay device(s) is processed; and
- a control system for controlling operation of the transport system such that each assay device is transferred between the different processing modules in a predetermined sequence, and such that a number of assay devices can be processed in different processing modules simultaneously, wherein one of the processing modules is an incubator comprising a housing and a set of assay device supports positioned within the housing; means for independently heating each assay device within the housing; and means for shaking the support relative to the housing.

9. An instrument according to claim 8, wherein the incubator has more than one support located in different vertical positions within a support unit, the support unit being vertically movable to bring a selected support into alignment with the instrument transport system.

10. An assay device processing instrument comprising:
- a plurality of different assay device processing modules, each module having an opening for receiving an assay device;
- a transport system including an assay device positioning assembly for transporting an assay device to each different processing module, the assay device positioning assembly being adapted to transfer the assay device into each different processing module via the opening to enable the assay device positioning assembly to transport another assay device to another processing module while the transferred assay device(s) is processed; and
- a control system for controlling operation of the transport system such that each assay device is transferred between the different processing modules in a predetermined sequence, and such that a number of assay devices can be processed in different processing modules simultaneously, wherein one of the processing modules is an assay device washing module comprising a wash fluid delivery probe and an aspirator probe mounted to a movable support, the aspirator probe being mounted at an angle to the vertical and the support being movable at substantially the same angle whereby when the aspirator probe is inserted into a well holder it is brought close to the side of the well holder.

11. An assay device processing instrument, comprising:

a plurality of assay device processing modules;

a transport system including an assay device positioning assembly for transporting an assay device to each processing module, the assay device positioning assembly being adapted to transfer the assay device to each module to enable the assay device positioning assembly to transport another assay device while the transferred assay device(s) is processed;

a control system for controlling operation of the transport system such that each assay device is transferred between the modules in a predetermined sequence, and such that a number of assay devices can be processed in different modules simultaneously, wherein the transport system further comprises a rail, the assay device positioning assembly mounted for movement along the rail, a first motor responsive to the control system to move the assay device positioning assembly into alignment with the respective processing modules, a support movably mounted to the rail, an arm for engaging an assay device and movably mounted to the support for movement laterally relative to the rail, and a second motor on the support for causing lateral movement of the arm, the second motor coupled to the arm by a rack and pinion arrangement.

12. An assay device processing instrument, comprising:

a plurality of assay device processing modules;

a transport system including an assay device positioning assembly for transporting an assay device to each processing module, the assay device positioning assembly being adapted to transfer the assay device to each module to enable the assay device positioning assembly to transport another assay device while the transferred assay device(s) is processed;

a control system for controlling operation of the transport system such that each assay device is transferred between the modules in a predetermined sequence, and such that a number of assay devices can be processed in different modules simultaneously, wherein the transport system further comprises a rail, the assay device positioning assembly mounted for movement along the rail, a first motor responsive to the control system to move the assay device positioning assembly into alignment with the respective processing modules, a support movably mounted to the rail, an arm for engaging an assay device and movably mounted to the support for movement laterally relative to the rail, a second motor on the support for causing lateral movement of the arm, and the arm is spring loaded and urged towards a retracted position.

13. An assay device processing instrument, comprising:

a plurality of different assay device processing modules, each module having an opening for receiving an assay device;

a transport system including an assay device positioning assembly for transporting an assay device to each different processing module, the assay device positioning assembly being adapted to transfer the assay device into each different processing module via the opening to enable the assay device positioning assembly to transport another assay device to another processing device while the transferred assay device(s) is processed;

a control system for controlling operation of the transport system such that each assay device is transferred between the different processing modules in a predetermined sequence, and such that a number of assay devices can be processed in different processing modules simultaneously, wherein one of the processing modules is an incubator comprising a housing and a set of assay device supports positioned within the housing, means for independently heating each assay device within the housing, and means for shaking the support relative to the housing, wherein the incubator has more than one support located in different vertical positions within a support unit, the support unit being vertically movable to bring a selected support into alignment with the instrument transport system.

14. An assay device processing instrument comprising:

a plurality of assay device processing modules;

a transport system including an assay device positioning assembly for transporting an assay device to each processing module, the assay device positioning assembly being adapted to transfer the assay device to each module to enable the assay device positioning assembly to transport another assay device while the transferred assay device(s) is processed; and a control system for controlling operation of the transport system such that each assay device is transferred between the modules in a predetermined sequence, and such that a number of assay devices can be processed in different modules simultaneously, wherein one of the processing modules is an assay device washing module comprising a wash fluid delivery probe and an aspirator probe mounted to a movable support, the aspirator probe being mounted at an angle to the vertical and the support being movable at substantially the same angle whereby when the aspirator probe is inserted into a well holder it is brought close to the side of the well holder.

* * * * *